United States Patent
Segawa et al.

(10) Patent No.: US 9,492,064 B2
(45) Date of Patent: Nov. 15, 2016

(54) CAPSULE ENDOSCOPE

(75) Inventors: Hidetake Segawa, Hachioji (JP); Satomi Kobayashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 2385 days.

(21) Appl. No.: 12/399,296

(22) Filed: Mar. 6, 2009

(65) Prior Publication Data
US 2009/0171149 A1 Jul. 2, 2009

Related U.S. Application Data (63) Continuation of application No. PCT/JP2007/066381, filed on Aug. 23, 2007.

(30) Foreign Application Priority Data

Sep. 7, 2006 (JP) ................... 2006-243167

(51) Int. Cl.
*A61B 1/06* (2006.01)
*A61B 1/04* (2006.01)
*A61B 1/00* (2006.01)

(52) U.S. Cl.
CPC ........... *A61B 1/041* (2013.01); *A61B 1/00181* (2013.01); *A61B 1/00183* (2013.01); *A61B 1/00193* (2013.01)

(58) Field of Classification Search
USPC ......................... 600/103, 109, 117–118, 160
See application file for complete search history.

(56) References Cited

U.S. PATENT DOCUMENTS

| 2005/0020880 A1* | 1/2005 | Miyake et al. ............... 600/121 |
| 2005/0171398 A1* | 8/2005 | Khait et al. .................. 600/102 |
| 2006/0004255 A1* | 1/2006 | Iddan et al. .................. 600/160 |
| 2006/0056828 A1* | 3/2006 | Iddan et al. .................... 396/14 |

(Continued)

FOREIGN PATENT DOCUMENTS

| JP | 2003-210394 | 7/2003 |
| JP | 2003-275170 | 9/2003 |

(Continued)

OTHER PUBLICATIONS

WO 02/095351 A3, dated Nov. 28, 2002 (Abstract and Search Report only).

(Continued)

*Primary Examiner* — Anhtuan T Nguyen
*Assistant Examiner* — Alexandra Newton
(74) *Attorney, Agent, or Firm* — Scully, Scott, Murphy & Presser, PC (57) ABSTRACT

A capsule endoscope includes a capsule casing and interior components housed therein whose total specific gravity is set such that the capsule casing floats in liquid introduced into a subject. The capsule endoscope also includes a gravity center position setting unit that sets a position of center of gravity of the capsule casing at a decentered position so that the capsule casing is stabilized in the liquid introduced into the subject without rotating except for rotation about an axis in a direction of the center of gravity; and an imager that takes an in-vivo image in a body cavity with an imaging field being set so that a surface of the liquid is out of view when the capsule casing floats in the liquid introduced into the subject in a stabilized posture.

17 Claims, 6 Drawing Sheets

(56) References Cited

U.S. PATENT DOCUMENTS

| | | | |
|---|---|---|---|
| 2007/0106112 A1* | 5/2007 | Gat et al. | 600/109 |
| 2007/0129624 A1* | 6/2007 | Gilad et al. | 600/407 |
| 2010/0010300 A1* | 1/2010 | Gilad | 600/109 |

FOREIGN PATENT DOCUMENTS

| | | |
|---|---|---|
| JP | 2004-121733 | 4/2004 |
| JP | 2004-529718 | 9/2004 |
| JP | 2005-198879 | 7/2005 |
| WO | WO 2004/058043 A2 | 7/2004 |
| WO | WO 2004/059568 A1 | 7/2004 |
| WO | WO 2005/060348 A2 | 7/2005 |

OTHER PUBLICATIONS

Extended Supplementary European Search Report dated Dec. 16, 2009.

* cited by examiner

CAPSULE ENDOSCOPE

CROSS-REFERENCE TO RELATED APPLICATIONS

This application is a continuation of PCT international application Ser. No. PCT/JP2007/066381 filed on Aug. 23, 2007 which designates the United States, incorporated herein by reference, and which claims the benefit of priority from Japanese Patent Applications No. 2006-243167, filed on Sep. 7, 2006, incorporated herein by reference.

BACKGROUND OF THE INVENTION

1. Field of the Invention

The present invention relates to capsule endoscopes capable of floating in liquid, for example, introduced into a subject and obtaining an in-vivo image.

2. Description of the Related Art

In recent years, capsule endoscopes having an imaging function and a radio communication function have appeared in the filed of endoscopes. A capsule endoscope of this type is typically configured to, for observation (examination), move inside the internal organs such as esophagus, stomach, and small intestine (within body cavities) by the organs' peristaltic movement during an observation period, after the endoscope is swallowed from a mouth of a person to be tested as a subject (human body) until the endoscope is naturally excreted from the body of the person to be tested, and sequentially take images using the imaging function.

International Publication No. 02/95351 (Japanese Patent Application Laid-Open No. 2004-529718) discloses a technique suitable for an observation of large intestine in which a capsule endoscope is swallowed together with liquid and floats in the liquid by making the specific gravity of the capsule endoscope same as that of liquid surrounding the endoscope or 1 which is the same as the specific gravity of water, so that the capsule endoscope can quickly reach the large intestine. Moreover, according to International Publication No. 02/95351, addressing the fact that only a portion close to the capsule endoscope can be observed when the capsule endoscope is close to a wall surface of a body cavity, it is possible to secure an observation view by making an observation with the capsule endoscope floating in the liquid, and thus realize the observation without an oversight. Japanese Patent Application Laid-Open No. 2004-121733 also refers to an observation in water.

SUMMARY OF THE INVENTION

A capsule endoscope according to an aspect of the present invention includes: a capsule casing and interior components housed therein whose total specific gravity is set such that the capsule casing floats in liquid introduced into a subject; a gravity center position setting unit that sets a position of center of gravity of the capsule casing at a decentered position so that the capsule casing is stabilized in the liquid introduced into the subject without rotating except for rotation about an axis in a direction of the center of gravity; and an imager that takes an in-vivo image in a body cavity with an imaging field being set so that a surface of the liquid is out of view when the capsule casing floats in the liquid introduced into the subject in a stabilized posture.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3-1 is a schematic diagram illustrating a modification in which a battery is used for a gravity center position setting unit;

FIG. 3-2 is a schematic diagram illustrating a modification in which an essential interior component is used for the gravity center position setting unit;

DETAILED DESCRIPTION OF THE PREFERRED EMBODIMENTS

The following describes embodiments of a capsule endoscope according to the present invention in detail with reference to the drawings. The present invention is not limited to these embodiments, and various modifications can be made without departing from the spirit of the invention.

The state that "the capsule casing floats in the liquid" as mentioned herein includes states that the capsule casing fully or partially sinks in the liquid.

First Embodiment

Figure 1:
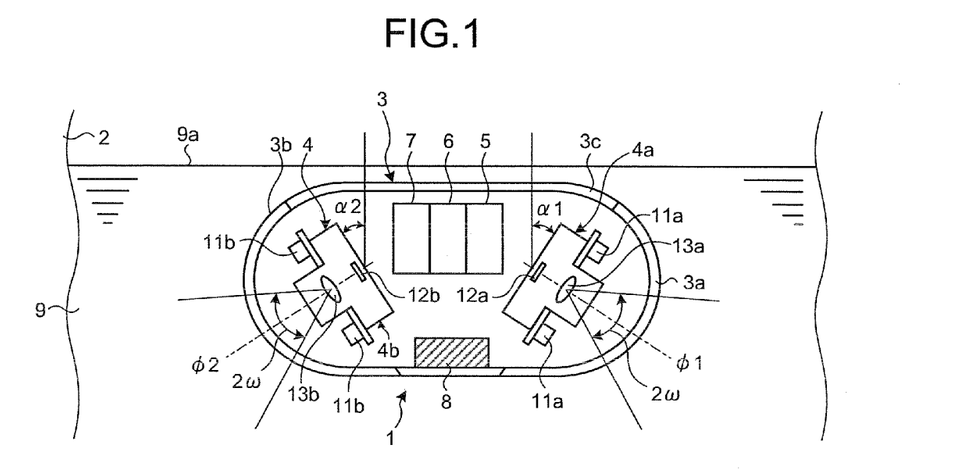
FIG. 1 is a schematic diagram illustrating a capsule endoscope according to a first embodiment of the present invention.

FIG. 1 is a schematic diagram illustrating a capsule endoscope according to a first embodiment of the present invention. A capsule endoscope 1 of the first embodiment is provided with a capsule casing 3 that is introducable into a body cavity of a subject 2, and interior components such as an imaging unit 4, a radio transmitting unit 5, a battery 6, an image processor 7, and a weight 8 that are housed in the capsule casing 3.

The capsule casing 3 is swallowable into the body cavity through a buccal cavity of the subject 2. The capsule casing 3, in which substantially semispherical end covers 3a and 3b each having transparency or translucency are elastically fitted with a tubular body cover 3c made of an opaque and colored material that blocks visible light, constitutes an exterior casing providing a liquid-tight seal.

The capsule endoscope 1 of the first embodiment floats in liquid 9 introduced into the subject 2 with sinking in the liquid 9. A total specific gravity of the capsule casing 3 including the interior components 4 to 8 housed therein is set to be greater than a specific gravity of the liquid 9. The liquid 9 is swallowable through the buccal cavity of the subject 2 and transparent to a wavelength of a light source used by the imaging unit 4 in image taking. In the first embodiment, drinking water whose specific gravity is about 1 is used as an example of such liquid.

Further, while the weight 8 is not an essential element in function of the capsule endoscope 1 unlike the components such as the imaging unit 4, the radio transmitting unit 5, the battery 6, and the image processor 7 that are necessary in the function of the capsule endoscope 1, the weight 8 is provided as a gravity center position setting unit that adjusts the specific gravity and sets a position of center of gravity at a decentered position so as to stabilize a posture of the capsule casing 3 floating in the liquid 9. In the first embodiment, the weight 8 is located at a position decentered on a short axis (in a direction crossing the center of a longitudinal axis) of the capsule casing 3 along an inner wall surface of the capsule casing 3. This consequently sets the position of the center of gravity at the position decentered on the short axis to the weight 8, and stabilizes the posture of the capsule casing 3 in such a manner that the capsule casing 3 is allowed to rotate only about an axis in a direction of the center of gravity and always floats horizontally in the liquid 9 in parallel with a surface 9a of the liquid. As a result, the posture in a vertical direction of the capsule casing 3 floating in the liquid 9 are determined such that the weight 8 is always positioned on a bottom side of the capsule casing 3.

Further, the imaging unit 4 is an imager that takes an in-vivo image in the body cavity, which is, in the first embodiment, configured as a binocular unit having two imaging optical systems 4a and 4b at both ends within the capsule casing 3 in a direction along the longitudinal axis. Each of the imaging optical systems 4a and 4b is provided with a plurality of light sources 11a and 11b such as LEDs that illuminate an imaging target, an imaging device 12a, 12b such as a CCD or CMOS imager that receives reflection of the light illuminated by the light sources 11a and 11b from the imaging target and takes an in-vivo image in the body cavity, and an imaging lens 13a, 13b that forms an optical image of the imaging target on the imaging device 12a, 12b. A maximum angle of view of the imaging optical systems 4a and 4b by which an image can be taken is considered to be 2ω.

Further, in the first embodiment, optical axes φ1 and φ2 of the imaging optical systems 4a and 4b are set to form an angle with the longitudinal axis of the capsule casing 3 so that imaging fields are directed downwardly from the capsule casing 3 that is horizontally stabilized and the posture in a vertical direction is determined. In the first embodiment, when inclination angles of the optical axes φ1 and φ2 of the imaging optical systems 4a and 4b are α1 and α2, respectively, the inclination angles α1 and α2 that are both directed downwardly and have the same sign are set so that relations of α1=α2=α and ω−α<0° are both satisfied. Satisfying these relations provides the imaging optical systems 4a and 4b, respectively, with the imaging fields being set so that the surface 9a of the liquid is always out of view. Further, the end covers 3a and 3b as described above are formed so as to correspond to the inclined positions of the imaging optical systems 4a and 4b.

Further, the image processor 7 is configured to carry out necessary image processing to the in-vivo image in the body cavity taken by the imaging device 12a, 12b, and the radio transmitting unit 5 is configured to wirelessly transmit data of the in-vivo image in the body cavity that have been taken by the imaging device 12a, 12b and processed by the image processor 7 as necessary to such as a receiver (not shown) provided outside the subject 2. The battery 6 is configured to supply power required for electric driving units such as the light sources 11a and 11b, and the imaging devices 12a and 12b that are housed in the capsule casing 3.

Next, an observation for the in-vivo image in the body cavity using the capsule endoscope 1 of the first embodiment is described. Basically, the observation is made in such a manner that the liquid 9 and the capsule endoscope 1 are swallowed through the buccal cavity, the stomach or large intestine as an observation site in the subject 2 is filled with the liquid 9, the capsule endoscope 1 floats in the filling liquid 9 that has filled with sinking in the liquid 9, and the in-vivo image in the body cavity is taken by the imaging optical systems 4a and 4b.

Figure 2:
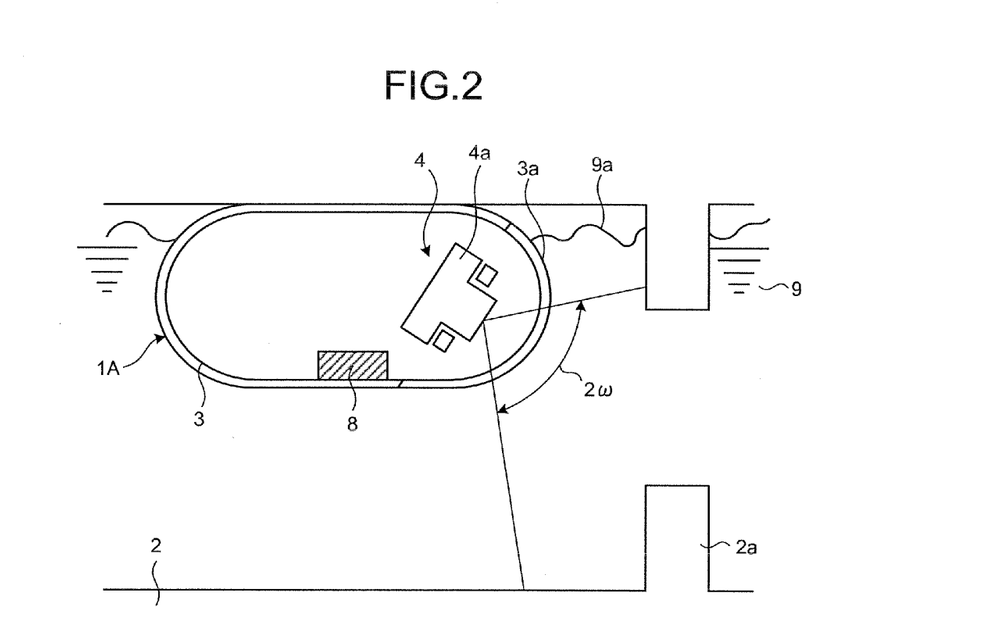
FIG. 2 is a schematic diagram illustrating an example of a monocular structure of the capsule endoscope shown in FIG. 1.

The center of gravity of the capsule endoscope 1 is decentered downwardly along the short axis by the weight 8. Accordingly, as shown in FIG. 1, the capsule endoscope 1 always floats in the liquid 9 introduced into the observation site in the horizontal posture parallel with the surface 9a of the liquid, and does not rotate except for rotation about an axis in a direction of the center of gravity. With such a stabilized floating posture, the imaging fields of the imaging optical systems 4a and 4b are directed downwardly so that the surface 9a of the liquid is out of view. This allows the imaging optical systems 4a and 4b to appropriately take the in-vivo image in the body cavity obliquely downward through the liquid 9 without being disturbed by such as reflection from the surface 9a of the liquid. Further, in a case in which an observation of such as a site within the large intestine is made, it is possible to acquire the in-vivo image in the body cavity avoiding the projection 2a, even when there is the projection 2a such as a fold that hinders the observation ahead as shown in FIG. 2.

In such an observation, taking the stomach as the observation site, for example, it is desirable that about 1 liter of the liquid 9 is swallowed. In addition to the fact that about 1 liter of liquid is appropriate as an amount that is swallowed for an examination, introducing the liquid 9 of this amount into the stomach allows the capsule endoscope 1 to observe an entirety of the stomach that is an internal organ having a large space, thereby reducing oversights. When changing the site observed by the capsule endoscope 1, timely turning the body position of the subject 2 who has swallowed the liquid 9 can change the position of the capsule endoscope 1 floating in the liquid 9. Such turning of the body position can reduce oversights by changing the site observed by the capsule endoscope 1. Moreover, the capsule endoscope 1 can make an observation by, after having first the liquid 9 be swallowed and then the capsule endoscope 1 be swallowed, taking images inside the stomach and the large intestine sequentially from an upper organ to the lower organ along with the movement (excretion) of the liquid 9 within the subject 2. Alternatively, the capsule endoscope 1 can adjust the position at which the capsule endoscope 1 floats in the body cavity by adjusting an amount of the liquid 9 to swallow by having the liquid 9 be gradually swallowed after the capsule endoscope 1.

In the embodiment 1, the capsule endoscope 1 is configured as a binocular type to reduce oversights by making an observation of the in-vivo image in the body cavity. However, as shown in FIG. 2, the present invention can also be applied to a capsule endoscope 1A structured as a monocular type by omitting the imaging optical system 4b.

Figure 31:
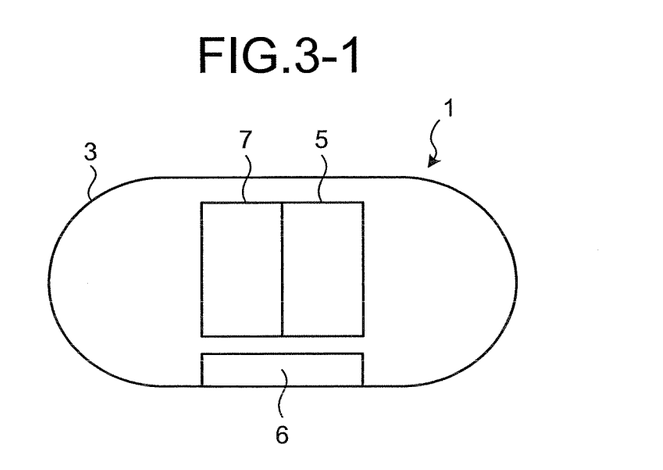
Figure 32:
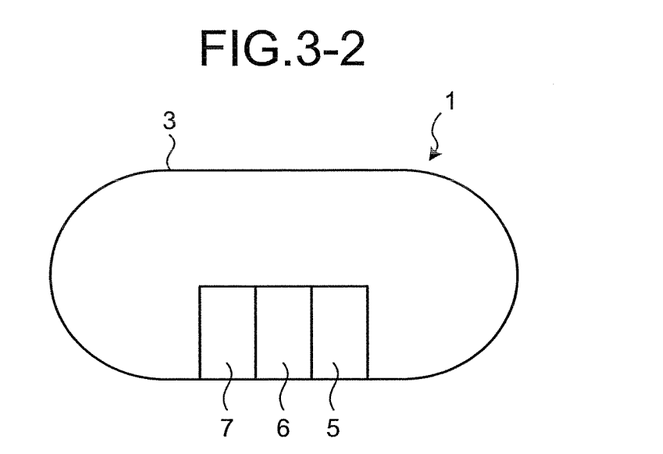

Further, in the first embodiment, the center of gravity of the capsule endoscope 1 is decentered by additionally providing the weight 8 that is not essential in function of the capsule endoscope 1 as the gravity center position setting unit. However, as shown in FIG. 3-1, the battery 6, for example, which is the component that is essential in function of the capsule endoscope 1 and that is relatively heavy can be used as the gravity center position setting unit instead of the weight 8, and the battery 6 can be provided at a position on the short axis and decentered from the longitudinal axis, thereby decentering the center of gravity of the capsule casing 3. Alternatively, as shown in FIG. 3-2, the center of gravity can be set at a position on the short axis and decentered from the longitudinal axis of the capsule casino 3 by providing the interior components that are essential in function of the capsule endoscope 1, such as the radio transmitting unit 5, the battery 6, and the image processor 7 on the same side with respect to the longitudinal axis. The above setting of the center of gravity also applies to cases of the embodiments that are described later.

Further, in the first embodiment, the imaging optical systems 4a and 4b are configured as a perspective optical system in which the optical axes φ1 and φ2 are inclined obliquely downward. However, the imaging optical systems 4a and 4b can be configured as a lateral optical system that takes an image immediately below with the inclination angles α1 and α2 at 90°.

Moreover, in the first embodiment, the case is described in which the center of gravity is set on the short axis using the weight 8, and the capsule endoscope 1 always floats horizontally in the liquid 9. However, it is not necessarily required that the capsule endoscope 1 float precisely in the horizontal posture. The capsule endoscope 1 can float somewhat obliquely with the center of gravity slightly decentering from the short axis in the direction of the longitudinal axis, as long as the inclination angles α1 and α2 of the imaging optical systems 4a and 4b satisfy the relation of $\omega-\alpha<0°$. Furthermore, it is not necessarily required that the respective inclination angles α1 and α2 of the imaging optical systems 4a and 4b be the same angle, and the inclination angles α1 and α2 can be different as long as the above relation is satisfied.

Second Embodiment

Figure 4:
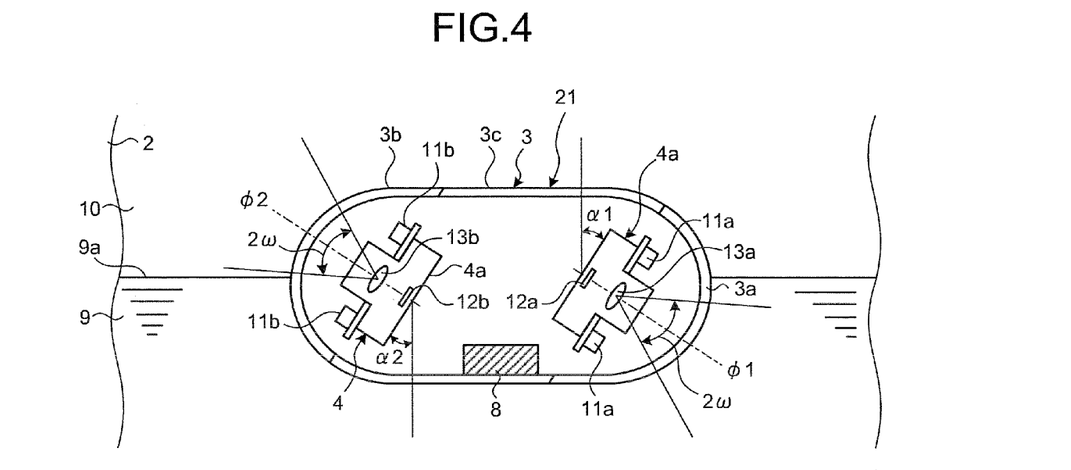
FIG. 4 is a schematic diagram illustrating a capsule endoscope according to a second embodiment of the present invention.

FIG. 4 is a schematic diagram illustrating a capsule endoscope according to a second embodiment of the present invention. The same numerals are used to denote the same components shown in FIG. 1. A capsule endoscope 21 of the second embodiment is provided with the capsule casing 3 that is introducable into the body cavity of the subject 2, and the interior components such as the imaging unit 4 to the weight 8 that are housed in the capsule casing 3. Here, the capsule endoscope 21 of the second embodiment is configured to float in the liquid 9 introduced into the subject 2 such that about a half of the capsule endoscope 21 floats on the surface 9a of the liquid 9. A total specific gravity of the capsule casing 3 including the interior components 4 to 8 housed therein is set to be smaller than the specific gravity of the liquid 9.

Further, while the weight 8 of the second embodiment is not essential in function of the capsule endoscope 21, the weight 8 is provided as the gravity center position setting unit that adjusts the specific gravity and sets the center of gravity at the position that is decentered so as to stabilize the posture of the capsule casing 3 floating on the surface 9a of the liquid 9. The weight 8 is provided at the position decentered on the short axis (in the direction crossing the center of the longitudinal axis) of the capsule casing 3 along the inner wall surface of the capsule casing 3, and this consequently sets the center of gravity at the position decentered on the short axis to the weight 8, and stabilizes the posture of the capsule casing 3 in such a manner that the capsule casing 3 is allowed to rotate only about an axis in the direction of the center of gravity and always floats horizontally in the liquid 9 in parallel with the surface 9a of the liquid. As a result, the posture in the vertical direction of the capsule casing 3 floating the surface 9a of the liquid are determined such that the weight 8 is always positioned on the bottom side of the capsule casing 3.

Further, the imaging unit 4 is configured as a binocular unit having the two imaging optical systems 4a and 4b with the inclined optical axes at the both ends within the capsule casing 3 in the direction along the longitudinal axis. In the capsule endoscope 21 of the second embodiment, when the inclination angles of the optical axes φ1 and φ2 of the imaging optical systems 4a and 4b are α1 and α2, respectively, the inclination angle α1 is directed obliquely downward into the liquid, and the inclination angle α2 is directed obliquely upward into air 10, and the inclination angles α1 and α2 that have different signs are set so that relations of $|\alpha1|=|\alpha2|=\alpha$ and $\omega-\alpha<0°$ are both satisfied. Satisfying these relations provides the imaging optical systems 4a and 4b with the imaging fields being set so that the surface 9a of the liquid is always out of view. Further, the end covers 3a and 3b as described above are formed so as to correspond to the inclined positions of the imaging optical systems 4a and 4b.

Next, an observation for the in-vivo image in the body cavity using the capsule endoscope 21 of the second embodiment is described. Basically, the observation is made in such a manner that the liquid 9 and the capsule endoscope 21 are swallowed through the buccal cavity, the stomach or large intestine as the observation site in the subject 2 is filled with the liquid 9, the capsule endoscope 21 floats on the surface 9a of the liquid 9 that has filled, and the in-vivo image in the body cavity is taken by the imaging optical systems 4a and 4b.

The center of gravity of the capsule endoscope 21 is decentered downwardly along the short axis by the weight 8. Accordingly, as shown in FIG. 4, the capsule endoscope 21 always floats on the surface 9a of the liquid 9 introduced into the observation site in the horizontal posture parallel with the surface 9a of the liquid, and does not rotate except for rotation about an axis in a direction of the center of gravity. With such a stable floating posture, the imaging field of the imaging optical system 4a is directed downwardly so that the surface 9a of the liquid is out of view. This allows the imaging optical system 4a to appropriately take the in-vivo image in the body cavity obliquely downward through the liquid 9 without being disturbed by such as reflection from the surface 9a of the liquid. Further, the imaging field of the imaging optical system 4b is directed upwardly so that the surface 9a of the liquid is out of view. This allows the imaging optical system 4b to appropriately take the in-vivo image in the body cavity obliquely upward through the air 10 without being disturbed by such as reflection from the surface 9a of the liquid. As described above, according to the capsule endoscope 21 of the second embodiment, the in-vivo images in the body cavity both through the liquid 9 and the air 10 can be appropriately observed without being disturbed by such as reflection from the surface 9a of the liquid.

In the second embodiment, the imaging optical systems 4a and 4b are configured as the perspective optical systems with the optical axes φ1 and φ2 are inclined. However, the imaging optical systems 4a and 4b can be configured as lateral optical systems with the inclination angles α1 and α2 being set to 90° and −90°, respectively, and taking images immediately below and immediately above.

Moreover, in the second embodiment, the case is described in which the center of gravity is set, using the weight 8, on the short axis and the capsule endoscope 1 always floats horizontally on the surface 9a of the liquid 9. However, it is not necessarily required that the capsule endoscope 21 float precisely in the horizontal posture. The capsule endoscope 21 can float somewhat obliquely with the center of gravity slightly decentering from the short axis in the direction of the longitudinal axis, as long as the inclination angles α1 and α2 of the imaging optical systems 4a and 4b satisfy the relation of ω−α<0°. Furthermore, it is not necessarily required that the respective inclination angles α1 and α2 of the imaging optical systems 4a and 4b be the same angle, and the inclination angles α1 and α2 can be different as long as the above relation is satisfied.

Third Embodiment

Figure 5:
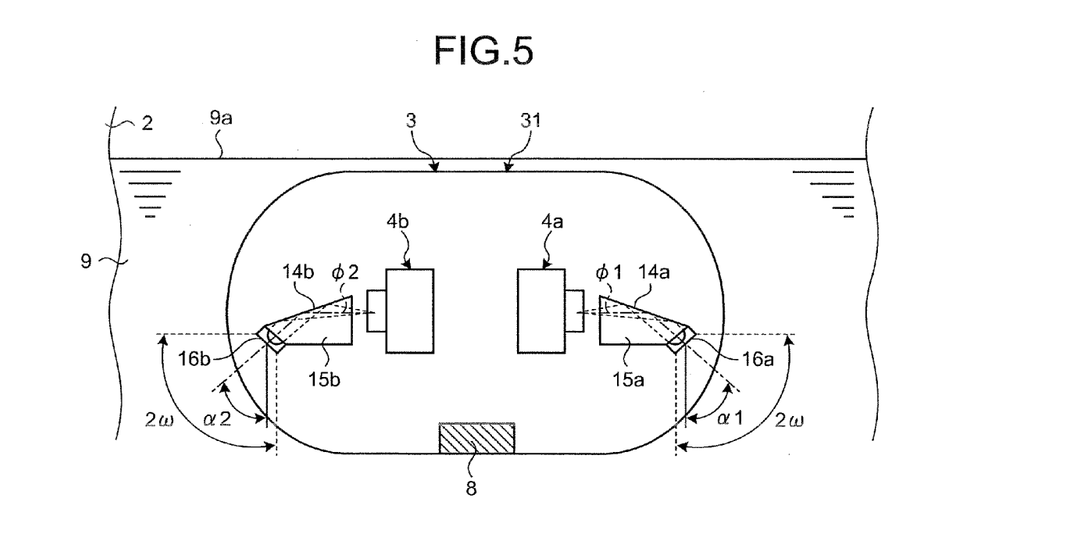
FIG. 5 is a schematic diagram illustrating a capsule endoscope according to a third embodiment of the present invention.

FIG. 5 is a schematic diagram illustrating a capsule endoscope according to a third embodiment of the present invention. The same numerals are used to denote the same components shown in FIG. 1. A capsule endoscope 31 of the third embodiment is provided with the capsule casing 3 that is introducable into the body cavity of the subject 2, and the interior components such as the imaging unit 4 to the weight 8 that are housed in the capsule casing 3. Here, the capsule endoscope 31 of the third embodiment is configured, similarly to the case of FIG. 1, to float in the liquid 9 introduced into the subject 2 with sinking in the liquid 9. A total specific gravity of the capsule casing 3 including the interior components 4 to 8 housed therein is set to be greater than a specific gravity of the liquid 9.

Further, the imaging unit 4 is configured as a binocular unit having the two imaging optical systems 4a and 4b at the both ends within the capsule casing 3 in the direction along the longitudinal axis. In the capsule endoscope 31 of the third embodiment, the optical axes φ1 and φ2 of the imaging optical systems 4a and 4b are set along the longitudinal axis of the capsule casing 3, and prisms 15a and 15b are provided as a reflecting member disposed ahead in the imaging directions of the imaging optical systems 4a and 4b and having reflecting planes 14a and 14b that incline directions of the imaging fields of the imaging optical systems 4a and 4b so that the surface 9a of the liquid is out of view. When the inclination angles in the directions of the imaging fields of the imaging optical systems 4a and 4b inclined by the reflecting planes 14a and 14b are α1 and α2, respectively, the inclination angles α1 and α2 that are both directed downwardly and have the same sign are set so that relations of α1=α2=α and ω−α<0° are both satisfied. Satisfying these relations provides the imaging optical systems 4a and 4b with the imaging fields being set so that the surface 9a of the liquid is always out of view.

Here, in a case in which the prisms 15a and 15b are provided as the reflecting members, in order to have light beams entering along the viewing direction with the inclination angle α (=α1=α2) enter into the imaging devices 12a and 12b without any loss, it is necessary to satisfy a total reflection condition in the reflecting plane of the prism whose refractive index n of glass material for the prism satisfies the following relation.

$$n \leq 1/\{\sin(\pi/2 - \alpha/2 - \omega)\}$$

It is desired that the inclination angles of the glass material and the reflecting planes 14a and 14b of the prisms 15a and 15b are determined so that the total reflection condition is satisfied. It is further desired to provide concave lenses 16a and 16b on incident planes of the prisms 15a and 15b, as appropriate glass material often cannot be found or the size of the prism often becomes larger when attempting to realize a broad angle of view.

The capsule endoscope 31 according to the third embodiment provides similar effects as provided by the capsule endoscope 1 according to the first embodiment. In particular, according to the third embodiment, the optical axes φ1 and φ2 of the imaging optical systems 4a and 4b are set along the longitudinal axis of the capsule casing 3, and this makes it possible to easily provide the effects only by adding such as the prisms 15a and 15b to a common structure of a binocular capsule endoscope and appropriately setting the directions of the imaging fields.

In the third embodiment, the prisms 15a and 15b are provided so as to incline the imaging fields of the imaging optical systems 4a and 4b obliquely downward. However, the imaging optical systems 4a and 4b can be configured to take an image immediately below with the inclination angle of the reflecting planes 14a and 14b at 45° and the inclination angles α1 and α2 at 90°.

Moreover, in the third embodiment, the case is described in which the center of gravity is set, using the weight 8, on the short axis and the capsule endoscope 31 always floats horizontally in the liquid 9 with sinking in the liquid 9. However, it is not necessarily required that the capsule endoscope 31 float precisely in the horizontal posture. The capsule endoscope 31 can float somewhat obliquely with the center of gravity slightly decentering from the short axis in the direction of the longitudinal axis, as long as the inclination angles α1 and α2 of the imaging optical systems 4a and 4b satisfy the relation of ω−α<0. Furthermore, it is not necessarily required that the respective inclination angles α1 and α2 of the imaging optical systems 4a and 4b in the directions of the imaging fields be the same angle, and the inclination angles α1 and α2 can be different as long as the above relation is satisfied.

Fourth Embodiment

Figure 6:
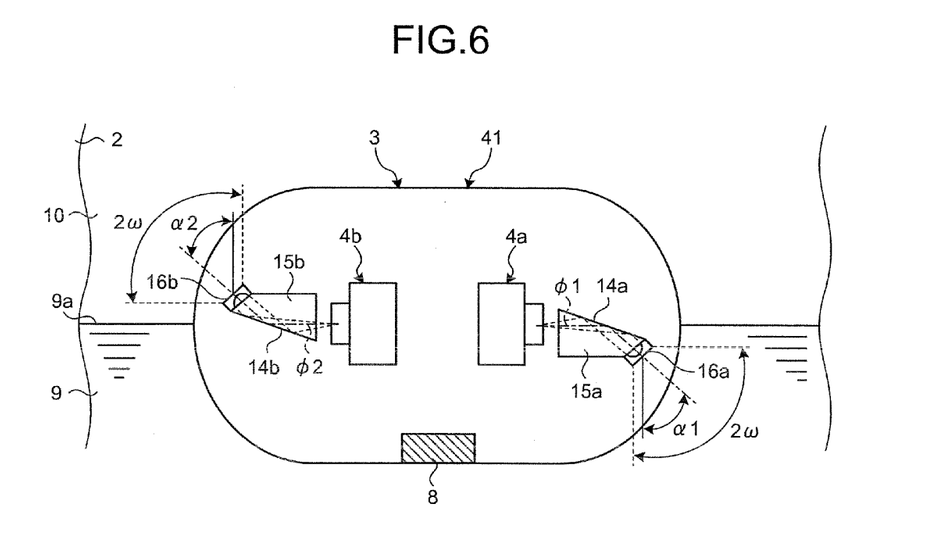
FIG. 6 is a schematic diagram illustrating a capsule endoscope according to a fourth embodiment of the present invention.

FIG. 6 is a schematic diagram illustrating a capsule endoscope according to a fourth embodiment of the present invention. The same numerals are used to denote the same components shown in FIG. 1, FIG. 4, and FIG. 5. A capsule endoscope 41 of the fourth embodiment is provided with the capsule casing 3 that is introducable into the body cavity of the subject 2, and the interior components such as the imaging unit 4 to the image processor 7, and the weight 8 that are housed in the capsule casing 3. Here, similarly to the case described in FIG. 4, the capsule endoscope 41 of the fourth embodiment is configured to float in the liquid 9 introduced into the subject 2 such that about a half of the capsule endoscope 41 floats on the surface 9a of the liquid 9. A total specific gravity of the capsule casing 3 including the interior components 4 to 8 housed therein is set to be smaller than the specific gravity of the liquid 9.

Further, while the weight 8 of the fourth embodiment is not essential in function of the capsule endoscope 41, the weight 8 is provided as the gravity center position setting unit that adjusts the specific gravity and sets the center of gravity at the position that is decentered so as to stabilize the posture of the capsule casing 3 floating on the surface 9a of the liquid 9. The weight 8 is provided at the position decentered on the short axis (in the direction crossing the center of the longitudinal axis) of the capsule casing 3 along the inner wall surface of the capsule casing 3, and this consequently sets the position of the center of gravity at the position decentered on the short axis to the weight 8, and stabilizes the posture of the capsule casing 3 in such a manner that the capsule casing 3 is allowed to rotate only about an axis in the direction of the center of gravity and always floats horizontally in the liquid 9 in parallel with the surface 9a of the liquid. As a result, the posture in the vertical direction of the capsule casing 3 floating the surface 9a of the liquid is determined such that the weight 8 is always positioned on the bottom side of the capsule casing 3.

Further, the imaging unit 4 is configured as a binocular unit having the two imaging optical systems 4a and 4b at the both ends within the capsule casing 3 in the direction along the longitudinal axis. In the capsule endoscope 41 of the fourth embodiment, the optical axes $\phi1$ and $\phi2$ of the imaging optical systems 4a and 4b are set along the longitudinal axis of the capsule casing 3, and prisms 15a and 15b are provided as a reflecting member disposed ahead in the imaging directions of the imaging optical systems 4a and 4b and having reflecting planes 14a and 14b that incline the directions of the imaging fields of the imaging optical systems 4a and 4b so that the surface 9a of the liquid is out of view. When the inclination angles in the directions of the fields of view of the imaging optical systems 4a and 4b inclined by the reflecting planes 14a and 14b are $\alpha1$ and $\alpha2$, respectively, the inclination angle $\alpha1$ is directed obliquely downward into the liquid, the inclination angle $\alpha2$ is directed obliquely upward into the air 10, and the inclination angles $\alpha1$ and $\alpha2$ that have different signs are set so that relations of $|\alpha1|=|\alpha2|=\alpha$ and $\omega-\alpha<0°$ are both satisfied. Satisfying these relations provides the imaging optical systems 4a and 4b with the imaging fields being set so that the surface 9a of the liquid is always out of view.

The capsule endoscope 41 according to the fourth embodiment provides similar effects as provided by the capsule endoscope 21 according to the second embodiment. In particular, according to the fourth embodiment, the optical axes $\phi1$ and $\phi2$ of the imaging optical systems 4a and 4b are set along the longitudinal axis of the capsule casing 3, and this makes it possible to easily provide the effects only by adding such as the prisms 15a and 15b to a common structure of a binocular capsule endoscope and appropriately setting the directions of the imaging fields.

In the fourth embodiment, the prisms 15a and 15b are provided so as to incline the imaging fields of the imaging optical systems 4a and 4b obliquely downward. However, the imaging optical systems 4a and 4b can be configured to take images immediately below and above with the inclination angle of the reflecting planes 14a and 14b at 45° and −45°, and the inclination angles $\alpha1$ and $\alpha2$ at 90° and −90°.

Moreover, in the fourth embodiment, the case is described in which the center of gravity is set, using the weight 8, on the short axis and the capsule endoscope 41 always floats horizontally on the surface 9a of the liquid 9. However, it is not necessarily required that the capsule endoscope 41 float precisely in the horizontally posture. The capsule endoscope 41 can float somewhat obliquely with the center of gravity slightly decentering from the short axis in the direction of the longitudinal axis, as long as the inclination angles $\alpha1$ and $\alpha2$ of the imaging optical systems 4a and 4b satisfy the relation of $\omega-\alpha<0°$. Furthermore, it is not necessarily required that the respective inclination angles $\alpha1$ and $\alpha2$ of the imaging optical systems 4a and 4b in the directions of the imaging fields be the same angle, and the inclination angles $\alpha1$ and $\alpha2$ can be different as long as the above relation is satisfied.

Fifth Embodiment

Figure 7:
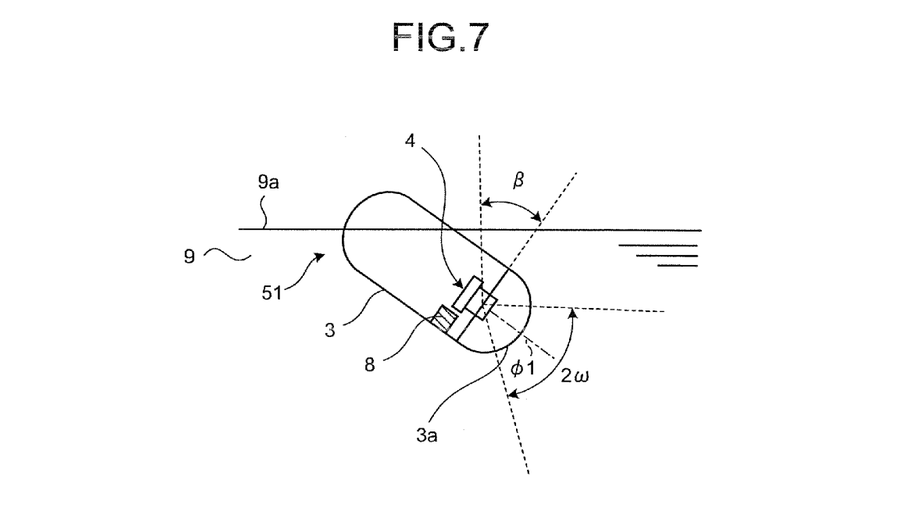
FIG. 7 is a schematic diagram illustrating a capsule endoscope according to a fifth embodiment of the present invention.

FIG. 7 is a schematic diagram illustrating a capsule endoscope according to a fifth embodiment of the present invention. The same numerals are used to denote the same components shown in FIG. 1 and such. A capsule endoscope 51 of the fifth embodiment is provided with the capsule casing 3 that is introducable into the body of the subject 2, and the interior components such as the imaging unit 4 to the weight 8 that are housed in the capsule casing 3. Here, the capsule endoscope 51 of the fifth embodiment is configured to float in the liquid 9 introduced into the subject 2 with floating on the surface of the liquid. A total specific gravity of the capsule casing 3 including the interior components 4 to 8 housed therein is set to be approximately equal to or smaller than a specific gravity of the liquid 9.

Further, the imaging unit 4 is configured as a monocular unit having the imaging optical system 4a on a side of the end cover 3a within the capsule casing 3, and the optical axis $\phi1$ of the imaging optical system 4a is set along the longitudinal axis of the capsule casing 3. Further, while the weight 8 of the fifth embodiment is not an essential element in function of the capsule endoscope 51, the weight 8 is provided as the gravity center position setting unit that adjusts the specific gravity and sets the position of the center of gravity at a position that is decentered so as to stabilize a posture of the capsule casing 3 floating in the liquid 9. The weight 8 is provided at the position decentered to the end cover 3a from the short axis (in a direction crossing the center of the longitudinal axis) of the capsule casing 3 along the inner wall surface of the capsule casing 3. This consequently sets the position of the center of gravity at the position decentered to the end cover 3a from the short axis to the weight 8, and stabilizes the posture of the capsule casing 3 in such a manner that the capsule casing 3 is allowed to rotate only about the axis in the direction of the center of gravity and always floats obliquely downward in the liquid 9. Here, the center of gravity is set such that the floating posture is stabilized in the liquid 9 with the capsule casing 3 inclined so as to satisfy the relation of $\omega-\beta<0°$, where the maximum angle of view of the imaging optical system 4a is $2\omega$ and the inclination angle of the capsule casing 3 with respect to the liquid level is $\beta$.

The capsule endoscope 51 according to the fifth embodiment also provides similar effects as provided by the capsule endoscope 1 according to the first embodiment. In particular, according to the fifth embodiment, since the optical axis $\phi1$ of the imaging optical system 4a is set along the longitudinal axis of the capsule casing 3, and this makes it possible to realize an observation in the body cavity without being affected by the surface 9a of the liquid only by modifying the setting of the position of the center of gravity by such as the weight 8 in a common structure of a monocular capsule endoscope.

In the fifth embodiment, the viewing direction is directed below the surface of the liquid (into the water). However, the viewing direction can be directed above the surface of the liquid (into the air).

Sixth Embodiment

Figure 8:
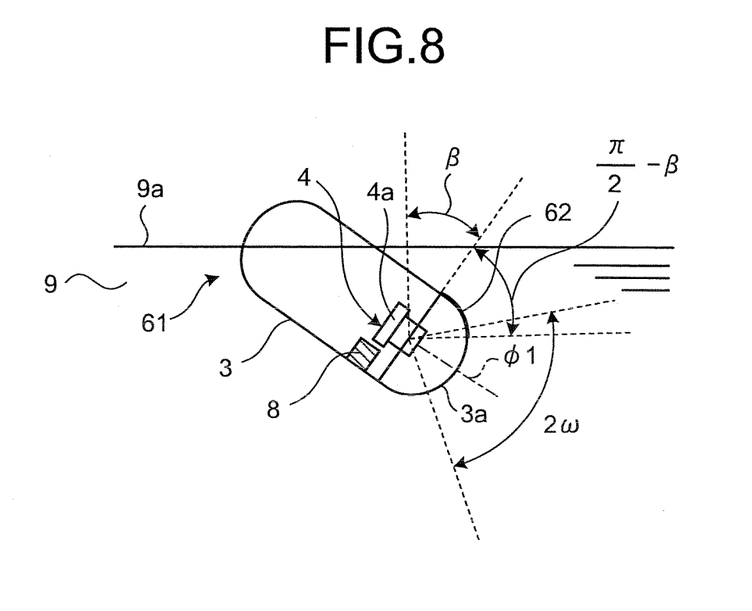
FIG. 8 is a schematic diagram illustrating a capsule endoscope according to a sixth embodiment of the present invention.
Figure 9:
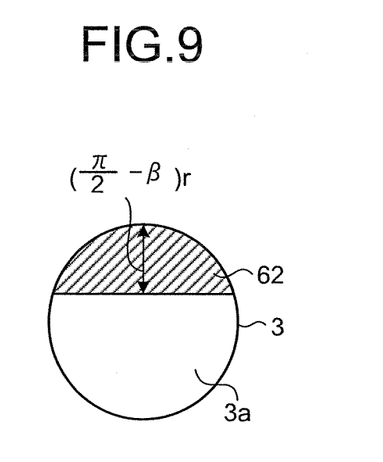
FIG. 9 is an elevational view of the capsule endoscope shown in FIG. 8.

FIG. 8 is a schematic diagram illustrating a capsule endoscope according to a sixth embodiment of the present invention, and FIG. 9 is an elevational view of this capsule endoscope. The same numerals are used to denote the same components shown in FIG. 1 and such. A capsule endoscope 61 of the sixth embodiment is provided with the capsule casing 3 that is introducable into the body cavity of the subject 2, and the interior components such as the imaging unit 4 to the weight B that are housed in the capsule casing 3. Here, the capsule endoscope 61 of the sixth embodiment is configured to float in the liquid 9 introduced into the subject 2 with floating on the surface of the liquid. A total specific gravity of the capsule casing 3 including the interior components 4 to 8 housed therein is set to be approximately equal to or smaller than a specific gravity of the liquid 9.

Further, the imaging unit 4 is configured as a monocular unit having the imaging optical system 4a on a side of the end cover 3a within the capsule casing 3, and the optical axis φ1 of the imaging optical system 4a is set along the longitudinal axis of the capsule casino 3. Further, while the weight 8 of the sixth embodiment is not an essential element in function of the capsule endoscope 61, the weight 8 is provided as the gravity center position setting unit that adjusts the specific gravity and sets the position of the center of gravity at a position that is decentered so as to stabilize a posture of the capsule casing 3 floating in the liquid 9. The weight 8 is provided at the position decentered to the end cover 3a from the short axis (in a direction crossing the center of the longitudinal axis) of the capsule casing 3 along the inner wall surface of the capsule casing 3. This consequently sets the position of the center of gravity at the position decentered to the end cover 3a from the short axis to the weight 8, and stabilizes the posture of the capsule casing 3 in such a manner that the capsule casing 3 is allowed to rotate only about the axis in the direction of the center of gravity and always floats obliquely downward in the liquid 9.

A light shield that restricts the imaging field so that the surface 9a of the liquid is out of view is provided ahead in the imaging direction of the imaging optical system 4a. In the capsule endoscope 61 of the sixth embodiment, as the light shield, a light shielding treatment, i.e. a dark paint 62 through which the light does not pass, is applied to a portion of the end cover 3a positioned within the imaging field of the capsule endoscope 61. Specifically, the treatment for the dark paint 62 is applied to an upper part of the end cover 3a shown by a shaded portion in FIG. 9 represented by a maximum length $(\pi/2-\beta)r$, where the maximum angle of view of the imaging optical system 4a is $2\omega$, the inclination angle of the capsule casing 3 with respect to the surface of the liquid is $\beta$, and a radius of the end cover 3a is r.

The center of gravity of the capsule endoscope 61 of the sixth embodiment is decentered downwardly to the end cover 3a from the short axis by the weight 8. Accordingly, as shown in FIG. 8, the capsule endoscope 61 always floats in an oblique posture with the predetermined inclination angle β to the surface 9a of the liquid 9 introduced into the observation site and does not rotate except for rotation about an axis in a direction of the center of gravity. With such a stable floating posture, the light shielding treatment of the dark paint 62 applied to the end cover 3a sets the imaging field of the imaging optical system 4a so that the surface 9a of the liquid is out of view. This allows the imaging optical system 4a to appropriately take the in-vivo image in the body cavity obliquely downward through the liquid 9 without being disturbed by such as reflection from the surface 9a of the liquid. In particular, this can be easily realized only by treating the predetermined portion of the end cover 3a with the treatment of the dark paint 62.

Figure 10:
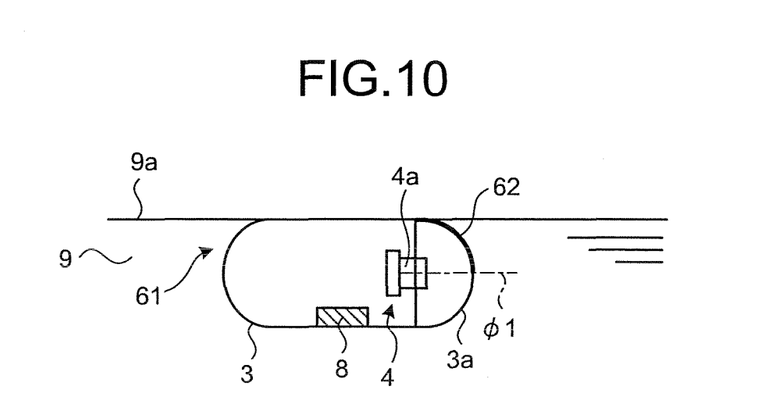
FIG. 10 is a schematic diagram illustrating a modification of the capsule endoscope according to the sixth embodiment.
Figure 11:
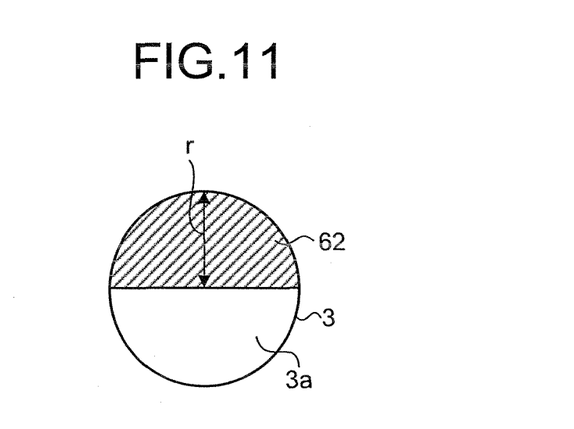
FIG. 11 is an elevational view of the capsule endoscope shown in FIG. 10.

A range of the treatment of the dark paint 62 applied to the end cover 3a varies according to the floating posture of the capsule endoscope 61. For example, if the capsule endoscope 61 with the specific gravity greater than the liquid 9 floats in the liquid 9 substantially in parallel with the surface 9a of the liquid as shown in FIG. 10, the light shielding treatment of the dark paint 62 can be applied to a range corresponding to the radius r of the end cover 3a as shown in FIG. 11.

Further, in the sixth embodiment, the case in which the dark paint 62 by means of the light shielding treatment is used as the light shield is described. However, although not especially shown in the drawing, a mechanical shield member that prevents the light that illuminates a range corresponding to the dark paint 62 from entering the imaging device 12a can be provided within the end cover 3a as the light shield.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope, comprising:
a capsule casing and interior components housed therein whose total specific gravity is set such that the capsule casing floats in liquid introduced into a subject;
a gravity center position setting unit that sets a position of center of gravity of the capsule casing at a decentered position so that the capsule casing is stabilized in the liquid introduced into the subject without rotating except for rotation about an axis in a direction of the center of gravity; and
an imager that takes an in-vivo image in a body cavity with an imaging field being set so that a surface of the liquid is out of view when the capsule casing floats in the liquid introduced into the subject in a stabilized posture;
wherein the imager includes an imaging optical system whose optical axis is inclined to a longitudinal axis of the capsule casing; and
the optical axis of the imaging optical system is inclined with respect to the surface of the liquid so as to satisfy a relation of:

$$\omega-\alpha<0°$$

where an inclination angle of the optical axis of the imaging optical system with respect to the surface of the liquid is $\alpha$, and a maximum angle of view is $2\omega$.

2. The capsule endoscope according to claim 1, wherein the imager is provided with a reflecting member that is disposed ahead in an imaging direction of an imaging optical system whose optical axis is set along a longitudinal axis of the capsule casing and that inclines a direction of the imaging field of the imaging optical system, the reflecting member including an optical axis of an imaging optical system that is inclined so that the surface of the liquid is out of view.

3. The capsule endoscope according to claim 2, wherein the optical axis of the imaging optical system is inclined with respect to the surface of the liquid so as to satisfy a relation of:

$$\omega-\alpha<0°$$

where an inclination angle of the optical axis of the imaging optical system with respect to the surface of the liquid is $\alpha$, and a maximum angle of view is $2\omega$.

4. The capsule endoscope according to claim 3, wherein
the specific gravity of the capsule casing is set such that the capsule casing floats in the liquid with sinking in the liquid, and
the imager includes two imaging optical systems whose inclination angles $\alpha 1$ and $\alpha 2$ are set to have the same sign.

5. The capsule endoscope according to claim 3, wherein
the specific gravity of the capsule casing is set such that the capsule casing floats in the liquid with floating on a surface of the liquid, and
the imager includes two imaging optical systems whose inclination angles $\alpha 1$ and $\alpha 2$ are set to have different signs.

6. The capsule endoscope according to claim 3, wherein the inclination angle $\alpha$ of the imaging optical system is 90°.

7. The capsule endoscope according to claim 1, wherein
the specific gravity of the capsule casing is set such that the capsule casing floats in the liquid with sinking in the liquid, and
the imager includes two imaging optical systems whose inclination angles $\alpha 1$ and $\alpha 2$ are set to have the same sign.

8. The capsule endoscope according to claim 1, wherein
the specific gravity of the capsule casing is set such that the capsule casing floats in the liquid with floating on a surface of the liquid, and
the imager includes two imaging optical systems whose inclination angles $\alpha 1$ and $\alpha 2$ are set to have different signs.

9. The capsule endoscope according to claim 1, wherein the inclination angle $\alpha$ of the imaging optical system is 90°.

10. The capsule endoscope according to claim 1, wherein the gravity center position setting unit sets the position of the center of gravity so that the capsule casing floats in the liquid and stabilized in a horizontal posture in which the longitudinal axis is substantially parallel with the surface of the liquid.

11. The capsule endoscope according to claim 1, wherein
the imager includes an imaging optical system whose optical axis is set along a longitudinal axis of the capsule casing, and
the gravity center position setting unit sets the position of the center of gravity so that the capsule casing floats in the liquid and stabilized in a posture in which the capsule casing is inclined so as to satisfy a relation of $\omega-\beta<0°$, where a maximum angle of view of the imaging optical system is $2\omega$ and an inclination angle of the capsule casing with respect to the surface of the liquid is $\beta$.

12. The capsule endoscope according to claim 1, wherein the imager is provided with a light shield that is disposed ahead in an imaging direction of an imaging optical system whose optical axis is set along the longitudinal axis of the capsule casing and that restricts the imaging field so that the surface of the liquid is out of view.

13. The capsule endoscope according to claim 12, wherein the light shield is configured as a shield member provided within the capsule casing.

14. The capsule endoscope according to claim 12, wherein the light shield is configured by applying a light shielding treatment to a portion of an end cover provided within the imaging field of the capsule casing.

15. The capsule endoscope according to claim 1, wherein the gravity center position setting unit is a weight.

16. The capsule endoscope according to claim 1, wherein the gravity center position setting unit is a battery.

17. A capsule endoscope, comprising:
a capsule casing and interior components housed therein whose total specific gravity is set such that the capsule casing floats in liquid introduced into a subject;
a gravity center position setting unit that sets a position of center of gravity of the capsule casing at a decentered position so that the capsule casing is stabilized in the liquid introduced into the subject without rotating except for rotation about an axis in a direction of the center of gravity; and
an imager that takes an in-vivo image in a body cavity with an imaging field being set so that a surface of the liquid is out of view when the capsule casing floats in the liquid introduced into the subject in a stabilized posture;
wherein the imager includes an imaging optical system whose optical axis is inclined to a longitudinal axis of the capsule casing; and
the optical axis of the imaging optical system is inclined with respect to the surface of the liquid so as to satisfy a relation of:

$$\omega-\omega<0°$$

where an inclination angle of the optical axis of the imaging optical system with respect to the surface of the liquid is $\alpha$, and a maximum angle of view is $2\omega$; and
wherein the gravity center position setting unit sets the position of the center of gravity so that the capsule casing floats in the liquid and stabilized in a horizontal posture in which the longitudinal axis is substantially parallel with the surface of the liquid.

* * * * *